United States Patent
Asselin et al.

[11] Patent Number: 4,470,990
[45] Date of Patent: Sep. 11, 1984

[54] 6,7,8,9-TETRAHYDRONAPHTHOL(1,2-b)FURAN-8-AMINE DERIVATIVES AND THEIR USE AS DOPAMINE RECEPTOR STIMULANTS

[75] Inventors: Andre A. Asselin, St. Laurent; Leslie G. Humber, Dollard des Ormeaux, both of Canada

[73] Assignee: Ayerst, McKenna & Harrison Inc., Montreal, Canada

[21] Appl. No.: 474,757

[22] Filed: Mar. 14, 1983

[51] Int. Cl.³ .................. A61K 31/34; C07D 307/92
[52] U.S. Cl. .................................. 424/267; 424/274; 424/285; 546/196; 548/425; 549/457
[58] Field of Search .............. 549/457; 546/196; 548/425; 424/267, 274, 285

[56] References Cited

U.S. PATENT DOCUMENTS 3,929,836 12/1975 Fothergill et al. ............... 549/467
4,110,339 8/1978 Bach et al. ...................... 424/274

FOREIGN PATENT DOCUMENTS 2740836 3/1979 Fed. Rep. of Germany .
7300871 7/1973 Netherlands .

OTHER PUBLICATIONS

Holt et al., Chem. Abst. 14156c, vol. 64 (1966).

L. B. Shagalov et al., Chem. Abstr. 91, 56747v (1979) for Kim. Geterotsikl. Soedin, (3), 360 (1979).
L. B. Shagalov et al., Chem. Abstr. 89, 146703r (1978) for Khim, Geterotsikl. Soedin, (5), 634 (1978).

*Primary Examiner*—Henry R. Jiles
*Assistant Examiner*—Bernard Dentz
*Attorney, Agent, or Firm*—Arthur E. Wilfond

[57] ABSTRACT

Herein is disclosed compounds of the formula

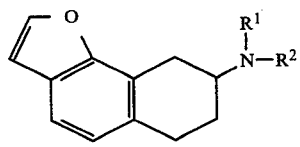

in which $R^1$ and $R^2$ each is hydrogen or lower alkyl or $R^1$ and $R^2$ together form an alkylene of the formula $(CH_2)_n$ wherein n is an integer from 4 to 6, therapeutically acceptable acid addition salts thereof, processes for their preparation, methods of using the compounds and pharmaceutical compositions. The compounds exhibit dopamine-receptor stimulating activity in a mammal and are useful for treating hyperprolactinemia, galactorrhea, amenorrhea, impotence, Parkinsonism, diabetes, acromegaly, hypertension and other central nervous system disorders.

7 Claims, No Drawings

6,7,8,9-TETRAHYDRONAPHTHO(1,2-B)FURAN-8-AMINE DERIVATIVES AND THEIR USE AS DOPAMINE RECEPTOR STIMULANTS

BACKGROUND OF THE INVENTION

This invention relates to novel 6,7,8,9-tetrahydronaphtho[1,2-b]furan-8-amine derivatives, to therapeutically acceptable acid addition salts thereof, to processes for their preparation, to methods of using the derivatives and to pharmaceutical compositions of the derivatives. These derivatives exhibit dopamine-receptor stimulating activity in a mammal. Thus, they can be useful for treating hyperprolactinemia, galactorrhea, amenorrhea, impotence, Parkinsonism, diabetes, acromegaly, hypertension and other central nervous system disorders which respond to dopamine-receptor simulation.

Although the naphtho[1,2-b]furan derivatives of this invention represent a novel tricyclic ring system, a number of benzindole derivatives are known and described, for example, L. B. Shagalov et al., Chem. Abstr., 91, 56747 v (1979) for Khim. Geterotsikl. Soedin., (3), 360 (1979); L. B. Shagalov et al., Chem. Abstr., 89, 146703 r (1978) for Khim. Geterotsikl. Soedin., (5), 634 (1978); Derwent Publications Ltd., Farmdoc 46000U for Netherland Patent No. 7,300,871, published July 30, 1973; and Derwent Publications Ltd., Farmdoc 24087B for German Offenlegenshift No. 2,740,836, published Mar. 22, 1979. The compounds described in the above reports have a benzindole ring system as contrasted to the naphtho[1,2-b]furan derivatives of this invention.

N. J. Bach and E. C. Kornfield, U.S. Pat. No. 4,110,339, Aug. 29, 1978 disclose tricyclic benzo[c]pyrroles which are dopamine agonists. These latter compounds are distinguished most readily from the compounds of this invention by having a fused tricyclic ring system with a nitrogen.

RELATED APPLICATIONS

Related hereto are our copending applications Ser. No. 312,464, filed Oct. 19, 1981 and Ser. No. 453,306, filed Dec. 27, 1982 directed to benzindol-8-amine derivatives. Also related hereto, is our U.S. Pat. No. 4,370,341, issued Jan. 25, 1983 and Derwent Publications Ltd., Farmdoc 55366E for European patent application 81305723.9, June 30, 1982. The instant application relates to naphtho[1,2-b]furan derivatives as contrasted to the benzindole derivatives of our other inventions.

SUMMARY OF THE INVENTION

The compounds of this invention are represented by formula I

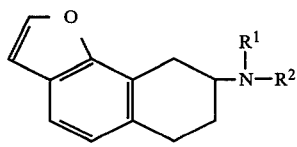

in which $R^1$ and $R^2$ each is hydrogen or lower alkyl or $R^1$ and $R^2$ together form an alkylene of the formula $(CH_2)_n$ wherein n is an integer from 4 to 6, or a therapeutically acceptable acid addition salt thereof.

A preferred group of compounds of this invention is represented by formula I in which $R^1$ and $R^2$ each is lower alkyl having one to three carbon atoms, or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to stimulate dopamine receptors in a mammal in need thereof by administering to the mammal an effective dopamine receptor stimulating amount of a compound of formula I or a therapeutically acceptable acid addition salt thereof. The compounds of this invention can be used in combination with an effective amount of an agent commonly used in the treatment of Parkinsonism and related disorders, particularly an agent selected from bromocriptine, lergotrile, levodopa, combination of levodopa and carbidopa, L-prolyl-L-leucylglycinamine and L-prolyl-N-methyl-D-leucylglycinaminde.

The compounds of formula I or a therapeutically acceptable acid addition salt thereof can be prepared by selecting a process from the group of:

(a) when a compound of formula I in which $R^1$ and $R^2$ are as defined herein is required, reacting a corresponding compound of formula II

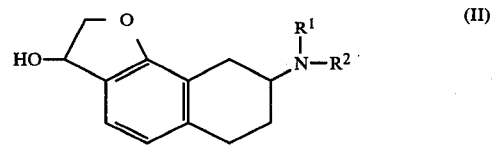

in which $R^1$ and $R^2$ are as defined herein with an aqueous mineral acid; and (b) when a therapeutically acceptable acid addition salt of a compound of formula I is required, reacting the compound of formula I with a therapeutically acceptable acid.

DETAILED DESCRIPTION OF THE INVENTION

The term "lower alkyl" as used herein means straight and branched chain alkyl radicals containing from one to five carbon atoms and includes methyl, ethyl, propyl, 1-methylethyl, butyl, 1,1-dimethylethyl and pentyl, unless stated otherwise.

The term "organic proton acceptor" as used herein means the organic bases or amines, for instance, triethylamine, pyridine, N-ethylmorpholine, 1,5-diazabicyclo[4.3.0]non-5-ene and the like.

The term "complex borohydride" as used herein means the metal borohydrides and includes, for example, sodium borohydride, sodium cyanoborohydride, potassium borohydride, lithium borohydride and zinc borohydride.

Also included in this invention are the stereochemical isomers of the compounds of formula I which result from asymmetric centers contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, methanesulfonic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The discovery in the mid-1960's of two major dopamine (DA) systems indicated that this neurotransmitter exerted control over a number of physiological functions. Against this background an interest arose to develop DA receptor agonists to study the function of the dopaminergic systems and to evaluate these agonists as possible therapeutic agents in Parkinson's disease and certain neuroendocrine disorders, for example, hyperprolactinemia, galactorrhea, amenorrhea, impotence, hypertension and other central nervous system disorders.

The dopamine-receptor stimulating activity of the compounds of formula I or a therapeutically acceptable acid addition salt thereof is demonstrated in standard pharmacological tests, for example, the antagonism of reserpine-induced catalepsy in mice described by A.M. Johnson et al., Br. J. Pharmac., 56, 59 (1976). In this test method, mice in groups of 10 were injected i.p. with reserpine, 5 mg/kg, 17 hr before the s.c. administration of the test compound. Catalepsy was assessed prior to drug administration and at 30 min, 1 and 2 hr after the test compound, and 1,2,3.5 and 5 hr after bromocriptine. Catalepsy was tested as follows: the mice were individually placed on a rubber stopper, 5 cm in diameter and 2½ cm high and observed for 3 min. Mice that remained on the corks during this period were considered to be cataleptic. The results are expressed as (a) dose-response curves, the values representing the percent antagonism of catalepsy during peak activity and (b) as $ED_{50}$'s vs time. Linearity and parallelism of the dose-response relationships were established by analysis of variance. In this test, the following compound of formula I was demonstrated to be an effective dopamine agonist, N,N-dipropyl-6,7,8,9-tetrahydronaphtho[1,2-b]furan-8-amine exhibited a peak $ED_{50}$ of $3.1 \pm 1.3$ milligram per kilogram of body weight upon s.c. administration in the prevention of reserpine-induced catalepsy.

The DA receptor agonists exert a variety of pharmacological effects, some of the most characteristic being the ones that occur in animals in which DA deficiency is brought about to mimic the Parkinsonian syndrome. An important model was developed by U. Ungerstedt, Acta. Physiol. Scand., Suppl. 367, 69–93 (1971) who, by means of unilateral injections of 6-hydroxydopamine (6-OHDA) into the DA pathway, could produce selective lesions of the ascending DA pathways on one side of the brain. Further refinement of this test is described by H. Corridi et al., J. Pharm. Pharmacol., 25, 409–412 (1973); C. J. Pycock and C. D. Marsden, Europ. J. Pharmacol., 47, 167 (1978); and K. Voith and J. R. Cummings, Can. J. Pharmacol., 54, 551 (1976).

Another useful test for dopamine receptor agonists is described by G. P. Smith and R. C. Young in "Advances in Neurology", Vol. 5, F. H. McDowell and A. Barbeau, Eds., Raven Press, New York, pp. 427–432 (1974). In this test, rats exhibit almost complete akinesia in an open field following the bilateral injection of 6-OHDA into the anterolateral hypothalamus. A dopamine receptor agonist can reverse this 6-OHDA-induced hypokinesia.

The above described test methods for dopamine receptor agonists show that the compounds of formula I are active as dopamine receptor agonists. The compounds, thus, can be used clinically in the treatment of hyperprolactinemia, galactorrhoea, amenorrhoea, impotence, diabetes, Parkinsonism, acromegaly, hypertension and other central nervous system disorders, which respond to dopamine-receptor stimulation.

The compounds of formula I of this invention are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as dopamine receptor agonists will vary with the form of administration and the particular compound chosen. Furthermore, it will vary with the particular host as well as the age, weight and condition of the host under treatment as well as with the nature and extent of the symptoms. Generally, treatment is initiated with small dosages. substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective dopamine receptor stimulating amount of the compounds for i.p. administration usually ranges from about 0.1 mg to about 250 mg per kilogram body weight per day in single or divided doses although as aforementioned variations will occur. However a dosage level that is in the range from about 0.1 to about 100 mg per kilogram body weight per day in single or divided doses is employed most desirably for i.p. administration in order to achieve effective results. For oral administration, effective amounts can range from about 0.5 to about 250 mg per kilogram body weight per day in single or divided doses preferably about 1.0 to 50 mg per kilogram of body weight per day.

The compound of formula I, or a therapeutically acceptable salt thereof, also can be used to produce beneficial effects in the treatment of Parkinsonism, hyperprolactinemia and related disorders when combined with a therapeutically effective amount of an agent commonly used in the treatment of Parkinsonism, hyperprolactinemia and related disorders. Such agents include, for example, apomorphine and its derivatives, piribedil and is derivatives, dopaminergic ergot derivatives, especially bromocriptine and lergotrile, 2-amino-6,7-dihydroxy-(1,2,3,4)-tetrahydronaphthalene (ADTN), levodihydroxyphenylalanine (levodopa), combination of levodopa with carbidopa, L-prolyl-L-leucylglycinamide (MIF) and its derivatives, especially L-prolyl-N-methyl-D-leucylglycinamide (pareptide), biperiden, cycrimine hydrochloride, procyclidine, trihexyphenidyl hydrochloride, benztropine, mesylate, chlorphenoxamine hydrochloride, diphenhydramine hydrochloride, orphenadrine hydrochloride, ethopropazine hydrochloride and the enzymes, monoamine oxidase B and catechol-O-methyl transferase. A combination of the foregoing agents can be substituted for a single agent. Suitable methods of administration, compositions and dosages of the agents are well known in the art; for instance, "Physcan Desk Reference", 36 ed., Medical Economics Co., Oradell, N.J., U.S.A., 1982. When used in combination, the compound of formula I, or its therapeutically acceptable salt, is administered as described previously.

The following reaction scheme illustrates a method of preparing the compounds of formula I in which $R^1$ and $R^2$ are as defined herein.

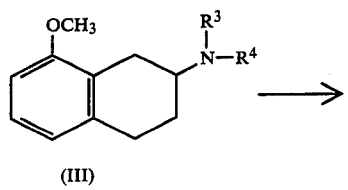

(III)

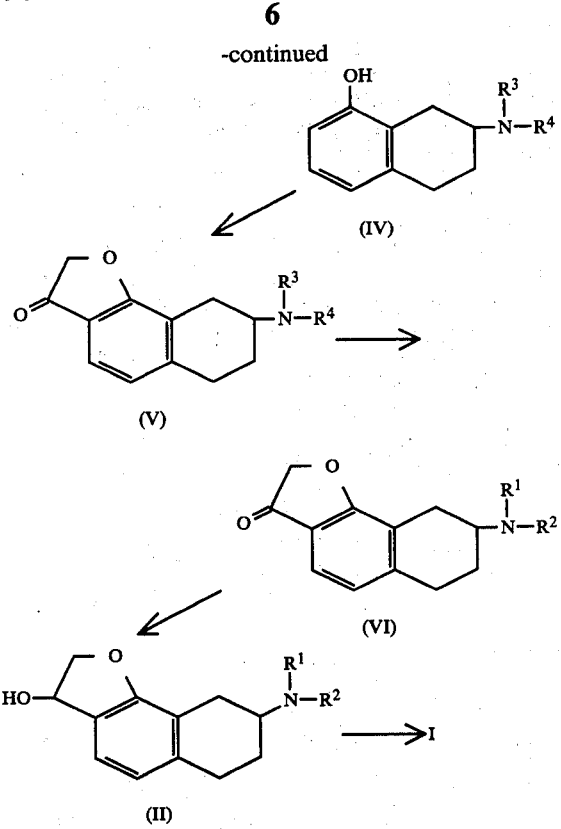

With reference to the above reaction scheme, 8-methoxy-2-tetralone is reacted with an amine of formula $HNR^3R^4$ and wherein $R^3$ and $R^4$ each is benzyl or lower alkyl or $R^3$ and $R^4$ together form an alkylene of the formula $(CH_2)_n$ wherein n is an integer from 4 to 6 in the presence of a catalytic amount of p-toluenesulfonic and with removal of water as it is formed. The reaction is conducted in toluene at about 100° to 110° C. for about 20 to 50 hours. Reduction of the resulting enamine with sodium borohydride gives the corresponding compound of formula III in which $R^3$ and $R^4$ are as defined herein. A number of compounds of formula III and methods for preparing them are described by D. E. Ames et al., J. Chem. Soc., 2636 (1965) and L.-E. Arvidsson et al., J. Med. Chem., 24, 921 (1981).

Demethylation of the compound of formula III in which $R^3$ and $R^4$ are as defined herein with boron tribromide in chloroform at about 10° to 30° C. for about 30 minutes to 5 hours followed by addition of anhydrous ethanol gives the corresponding compound of formula IV in which $R^3$ and $R^4$ are as defined herein. A compound of formula IV and a method for preparing it is described by L.-E. Arvidsson et al., cited above.

Conversion of the compound of formula IV in which $R^3$ and $R^4$ are as defined herein to the corresponding compound of formula V in which $R^3$ and $R^4$ are as defined herein is achieved by the following steps. In the first step, the compound of formula IV is reacted with about two to three molar equivalents of boron trichloride in dichloromethane at about 0° to 5° C. A mixture of the resulting solution, about two to three molar equivalents of chloroacetonitrile and about one to two molar equivalents of aluminum trichloride is stirred at about 20° to 30° C. for about 20 to 30 hours. The resulting mixture is then treated with dilute aqueous hydrochloric acid at about 20° to 30° C. for about one hour and basified with dilute ammonium hydroxide. The solution is extacted with a water immiscible organic solvent and the extract is evaporated. A solution of the residue in an inert organic solvent, preferably chloroform, and an organic proton acceptor, preferably triethylamine, is heated about 50° to 75° C. for about one to five hours to obtain the compound of formula V in which $R^3$ and $R^4$ are as defined herein.

Hydrogenation of the compound of formula V in which $R^3$ is benzyl and $R^4$ is benzyl or lower alkyl in the presence of a noble metal hydrogenation catalyst, preferably palladium on carbon, in an inert solvent, for example, methanol or ethanol, gives the corresponding compound of formula VI in which $R^1$ is hydrogen and $R^2$ is hydrogen or lower alkyl.

The componds of formula V in which $R^3$ and $R^4$ each is lower alkyl or $R^3$ and $R^4$ together form an alkylene of formula $(CH_2)_n$ are equivalent to the corresponding compounds of formula VI in which $R^1$ and $R^2$ are the same as the latter definitions of $R^3$ and $R^4$.

Reduction of the compound of formula VI in which $R^1$ and $R^2$ are as defined herein with a complex borohydride, preferably sodium borohydride, in an inert solvent, preferably a mixture of dioxane and water, at about 20° to 100° C. for about 30 minutes to five hours gives the corresponding compound of formula II in which $R^1$ and $R^2$ are as defined herein.

Treatment of the compound of formula II in which $R^1$ and $R^2$ are as defined herein with an aqueous mineral acid affords the corresponding compound of formula I in which $R^1$ and $R^2$ are as defined herein. Suitable aqueous mineral acids can be selected from 5 to 20% hydrochloric acid, hydrobromic acid, sulfuric acid and phosphoric acid. About 5 to 15% hydrochloric acid is preferred. The reaction is conducted at about 10° to 50° C. for about one to five hours The following example illustrates further this invention.

EXAMPLE

N,N-Dipropyl-6,7,8,9-tetrahydronaphtho[1,2-b]furan-8-amine (I: $R^1$ and $R^2$=propyl)

5,6,7,8-Tetrahydro-7-(dipropylamino)-naphthalenol hydrobromide [5.90 g, 18.0 mmol, described by L.-E. Arvidsson et al., J. Med. Chem. 24, 921 (1981)] was added portionwise as a solid to an ice-cold solution of boron trichloride in dichloromethane (43 mL, 1M solution). To the clear solution was added successively chloroacetonitrile (2.74 mL, 43 mmol) and aluminum trichloride (2.88 g, 22 mmol). A precipitate formed after 0.5 hour. The suspension was left stirring at room temperature overnight. Then, ice-water and 10% hydrochloric acid (20 mL) were added and the mixture was stirred vigorously for 1 hour at room temperature. It was made basic with dilute ammonium hydroxide and shaken with chloroform. The emulsion was filtered through diatomaceous earth, and washed with chloroform. The organic layer was separated, dried and evaporated to dryness. The residue was taken up in chloroform (150 mL) and triethylamine (10 mL) was added. The solution was refluxed on a steam bath for 2 hours, and evaporated to dryness. The residue was partitioned between diethyl ether and dilute ammonium hydroxide. The ether phase was washed with water, dried and evaporated to give N,N-dipropyl-2,3,6,7,8,9-hexahydro-3-oxonaphtho[1,2-b]furan-8-amine as a crude pink solid (5.5 g), and was used as such for the next step. An analytical sample was passed through a column of silica gel and eluted with chloroform and a mixture of acetone and chloroform (1:9) to give an oil which solidified on standing: mp 56°–64° C. and NMR (CDCl$_3$)δ 0.87 (t, 6H), 1.47 (m, 6H), 2.48 (t, 4H), 2.70 (m, 1H), 2.87 (m, 4H), 4.59 (s, 2H), 6.27 (d, 1H) and 7.37 (d, 1H).

To a solution of the latter compound (5.5 g (crude), 18.0 mmol) in dioxane (100 mL) and water (10 mL), sodium borohydride (2.5 g, 0.06 mol) was added portionwise at room temperature. The reaction mixture was refluxed for 2 hours and evaporated. Water was added to the residue and the mixture was extracted with diethyl ether. The ether extracts were dried and evaporated to give a crude pink oil (5.5 g) of 8-(dipropylamino)-2,3,6,7,8,9-hexahydronaphtho[1,2-b]furan-3-ol, and was used as such in the next step. An analytical sample (350 mg) was rapidly filtered through a column of activated magnesium silicate using diethyl ether to give a colorless oil (290 mg): NMR (CDCl$_3$)δ 0.87 (t, 6H), 1.44 (m, 6H), 1.90 (s, 1H), 2.56 (t, 4H), 2.80 (m, 4H), 4.54 (m, 2H), 5.25 (t, 1H), 6.63 (d, 1H) and 7.11 (d, 1H).

A solution of the latter compound (5.2 g (crude), 18.0 mmol) in 10% hydrochloric acid (30 mL) was allowed to stand at room temperature for 2 hours. The reaction mixture was made basic with concentrated ammonium hydroxide and extracted with diethyl ether. The organic extracts were dried and evaporated to give a pink oil (3.8 g) which was filtered through a column of activated magnesium silicate using a mixture of petroleum ether and diethyl ether (1:1) to give a colorless oil (3.2 g) of the title compound. The oil was treated with a solution of HCl in diethyl ether to afford a salt which was crystallized from chloroform and diethyl ether to give the hydrochloride salt of the title compound (3.2 g): mp 224°–226° C.; NMR (CDCl$_3$)δ 1.05 (t, 6H), 2.0 (m, 6H), 3.05 (m, 9H), 6.7 (d, 1H), 6.95 (d, 1H), 7.40 (d, 1H), 7.55 (d, 1H) and 12.3 (br, 1H).

In the same manner but replacing 5,6,7,8-tetrahydro-7-(dipropylamino)-1-naphthalenol with an equivalent amount of 5,6,7,8-tetrahydro-7-(1-piperidinyl)-1-naphthalenol, 6,7,8,9-tetrahydro-8-(1-piperidinyl)-naphtho[1,2-b]furan is obtained.

We claim:

1. A compound of the formula

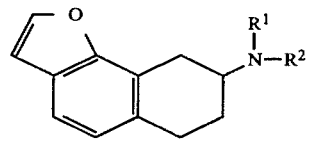

in which $R^1$ and $R^2$ each is hydrogen or lower alkyl or $R^1$ and $R^2$ together form an alkylene of the formula $(CH_2)_n$ wherein n is an integer from 4 to 6, or a therapeutically acceptable acid addition salt thereof.

2. A compound of claim 1 wherein $R^1$ and $R^2$ each is lower alkyl having one to three carbon atoms, or a therapeutically acceptable acid addition salt thereof.

3. N,N-Dipropyl-6,7,8,9-tetrahydronaphtho[1,2-b]furan-8-amine, a compound of claim 2 wherein $R^1$ and $R^2$ are propyl.

4. A pharmaceutical composition, which comprises an effective dopamine receptor stimulating amount of compound of claim 1, or a therapeutically acceptable acid addition salt thereof, and a pharmaceutically acceptable carrier therefor.

5. A method of stimulating dopamine-receptors in a mammal in need thereof, which comprises administering to said mammal an effective dopamine receptor stimulating amount of a compound of claim 1 or a therapeutically acceptable acid addition salt thereof.

6. A compound of the formula

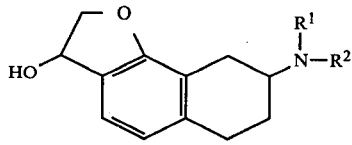

in which $R^1$ and $R^2$ each is hydrogen or lower alkyl or $R^1$ and $R^2$ together form an alkylene of the formula $(CH_2)_n$ wherein n is an integer from 4 to 6.

7. A compound of the formula

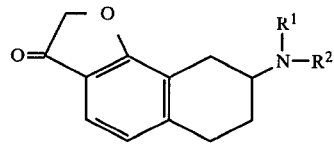

in which $R^1$ and $R^2$ each is hydrogen or lower alkyl or $R^1$ and $R^2$ together form an alkylene of the formula $(CH_2)_n$ wherein n is an integer from 4 to 6.

* * * * *